United States Patent
Shrivastava (12)

(10) Patent No.: US 6,254,899 B1
(45) Date of Patent: Jul. 3, 2001

(54) PLANT EXTRACT COMPOSITIONS, METHOD OF PREPARATION, AND PHARMACEUTICAL COMPOSITIONS CONTAINING THEM

(75) Inventor: Ravi Shrivastava, Puy de Dôme (FR)

(73) Assignees: Laboratoires Remilea, Issoire; Shrivastava, Cebazat, both of (FR)

(*) Notice: Subject to any disclaimer, the term of this patent is extended or adjusted under 35 U.S.C. 154(b) by 0 days.

(21) Appl. No.: 09/380,371

(22) PCT Filed: Mar. 3, 1997

(86) PCT No.: PCT/FR97/00370

§ 371 Date: Sep. 1, 1999

§ 102(e) Date: Sep. 1, 1999

(87) PCT Pub. No.: WO98/39018

PCT Pub. Date: Sep. 11, 1998

(51) Int. Cl.$^7$ .......................... A61K 35/78; A61K 31/60; C01F 7/02

(52) U.S. Cl. .......................... 424/769; 424/630; 424/631; 424/641; 424/682; 424/764; 514/159

(58) Field of Search ................. 424/195.1, 630, 424/631, 641, 617, 677, 682, 764, 769; 514/159

(56) References Cited

U.S. PATENT DOCUMENTS 4,755,384 * 7/1988 Mallasz ................................. 424/131
4,962,121 * 10/1990 Hamberger et al. ................. 514/419
5,538,959 * 7/1996 Mauskop ............................... 514/165

FOREIGN PATENT DOCUMENTS

96/22774 * 8/1996 (WO).

OTHER PUBLICATIONS

Product Alert Abstract: Nature's Bounty Herbal Harvest Herbal Nutr. Supplement, Feb. 1994.*
Product Alert Abstract: Alvita Herbal RemeTeas, Jul. 1996.*
Product Alert Abstract: Herbs for Kids Liquid Extract, Jun. 1993.*
Castleman, M. The Healing Herbs, Rodale Press, Emmaus, PA. pp. 173–176 & 369–371, 1991.*
PDR for Herbal Medicines, Medical Economics Co., Montvale, NJ. pp. 1111–1112, 1998.*
Database WPI, Section Ch, Week 9518, Derwent Publications Ltd., London, GB; Class B04, An 95–139371. XP002044282 & WO 95 08318 A (PEIDUS V N), Mar. 30, 1995.

* cited by examiner

Primary Examiner—Christopher R. Tate
(74) Attorney, Agent, or Firm—Browdy and Neimark

(57) ABSTRACT

The invention concerns a composition of salicoid (*Salix alba* extract) and parthenoid (*Tanacetum parthenium* extract), or of plants of plant extracts containing these two active principles, its use in a method for treatment of the human or animal body by therapy or for the preparation of a medicine in particular for treating migraine, and compositions particularly pharmaceutical containing them. The composition also preferably comprises a heavy metal element such as copper, zinc and/or magnesium.

13 Claims, No Drawings

PLANT EXTRACT COMPOSITIONS, METHOD OF PREPARATION, AND PHARMACEUTICAL COMPOSITIONS CONTAINING THEM

CROSS REFERENCE TO RELATED APPLICATION

The present application is the national stage under 35 U.S.C. 371 PCT/FR97/00370, filed Mar. 3, 1997.

The present invention relates to new compositions of plant extracts, their preparation process, their use as medicaments and the pharmaceutical compositions containing them.

Migraines affect approximately 10% of the French population on a regular basis. This illness predominantly affects women (two women to every one man).

Treatments for migraine are essentially symptomatic; none is actually curative. Several reasons explain the lack of discovery of an effective anti-migrainous medicament. The main difficulty is that the intimate factors triggering the onset of migraine are not fully known. However, hypotheses have been put forward with regard to the role of neuronal receptors (serotonin, dopamine, histamine), prostaglandins, noradrenergic receptors (central and peripheral), stress, diet, the effects of pollution.

All these elements probably contribute to the triggering of a migrainous attack, but do not in themselves explain the phenomenon. In the absence of scientific data on the migraine mechanism, the treatment can only be symptomatic for the moment.

Dihydro-ergotamine, prostaglandin inhibitors (aspirin), analgesics (paracetemol), calcium channel blockers, β-blockers and the other inhibitory molecules of the 5HT receptor such as sumatriptan constitute the symptomatic treatments for this illness.

These medicaments, of chemical origin, are known to have undesirable or even toxic effects (for example the hepatotoxic effect of paracetemol and aspirin), in particular in the case of chronic use. Moreover, because of their effectiveness and their low toxicity, the new coming products are usually expensive.

Active compounds for combatting migraine are always being sought. Moreover, sufferers are increasingly favouring products of natural origin.

The barks of white willows (*Salix alba*) are used, particularly in France, for the treatment by oral route of light fevers and colds, in the case of pain, and by oral and local route for pains in joints, tendinitis and sprains. The active ingredients concerned would be salicoids.

The aerial part of the Feverfew (*Tanacetum parthenium*) is used for the treatment by oral route of painful periods and in the prevention of migrainous attacks. The active ingredients concerned would be parthenoids.

Thus the Applicant discovered with astonishment that compositions of salicoids (i.e. salicin and its derivatives) and parthenoids, or plants or plant extracts containing these two active ingredients, in particular combined with a metal chosen preferably from copper, zinc or magnesium in a trace element state, or with riboflavin, were endowed with remarkable anti-inflammatory, analgesic and anti-migrainous properties.

For this reason, a subject of the present invention is a new composition of a salicoid and a parthenoid, or plants or plant extracts containing these two active ingredients. A preferred composition comprises a plant extract of the Tanacetum genus and a plant extract of the Salix genus.

"Plant extract" is understood in general to mean both plants and parts of plants, for example and preferably dried or dehydrated and ground, or also extracts of such plants or parts of plants obtained using at least one aqueous and/or organic solvent and being present in a standard liquid or in particular solid form used in pharmacy or dietetics.

The plant of the Tanacetum genus can be for example *Matricaria pyrethrum, Leucanthenum parthenium* and preferably *Tanacetum parthenium* also called *Matricaria chamomilla*. The aerial parts of this plant, dried and ground, are preferably used; such extracts are for example those marketed by the company BIOSPHERE 99 (Vic le Comte—FRANCE) under the reference BIO 3010.

The plant of the Salix genus can be *Salix cinerea* for example and preferably *Salix alba*. The bark of this plant, dried and ground, is preferably used; such extracts are for example those marketed by the company BIOSPHERE 99 under the reference BIO 3021.

A preferred composition above is characterized in that it contains in addition riboflavin, zinc, magnesium or preferably copper in a trace element state, i.e. the metal is used in low or very low proportions for example less than 1 part per 100, preferably less than 1 part per 300, in particular less than 1 part per 1000 relative to the weight of the other constituents.

The copper used can be presented in particular in the form of copper salts, in particular cupric salts ($Cu^{++}$), for example in the form of mineral salts such as copper sulphate, and very particularly salified in the form of organic salts, preferably in the form of gluconates. The same applies for zinc and magnesium.

The above compositions in which the plant of the Tanacetum genus is *Tanacetum parthenium* and the plant of the Salix genus is *Salix alba* are particularly preferred.

Among the compositions of the invention, those in which the extracts used are the dry extracts of parts of plants, dried and ground, in particular those in which the extracts used are the aerial parts of *Tanacetum parthenium*, dried and ground and those in which the extracts used are the bark of *Salix alba*, dried and ground, can also be mentioned.

A preferred composition above is characterized in that it contains, if referring to extracts of the above type and taking only the said extracts into account, 10 to 90% by weight of Tanacetum parthenium extract and 10 to 90% by weight of *Salix alba* extract.

The compositions which are a subject of the present invention have very useful pharmacological properties. They are endowed in particular with remarkable anti-inflammatory, analgesic and anti-migrainous properties.

These properties are illustrated hereafter in the experimental part. They justify the use of the compositions described above as medicaments.

For this reason, a subject of the invention is also the compositions of a plant extract of the Tanacetum genus and a plant extract of the Salix genus, for their use in a method for the therapeutic treatment of the human or animal body, i.e. as a medicament.

The medicaments according to the present invention are used for example in both the curative and preventative treatment of rheumatisms, anti-inflammatory pathologies, vascular pathologies, in particular arterial hypertension or vascular spasms and cardiac pathologies, in particular tachycardias.

They are also used in both the curative and preventative treatment of migraines.

The usual dose, variable according to the patient treated and the affection in question can be, for example, 100 mg to 1000 mg per day, by oral route in man, of the aerial parts, dried and ground, of *Tanacetum parthenium* with 300 mg to 1000 mg of the bark, dried and ground, of *Salix alba* and with 0.05 mg to 2.50 mg of copper in state of copper ions, administered for 7 to 30 days for the curative or preventative treatment of migraines.

A subject of the invention is also the pharmaceutical compositions which contain at least one previously-mentioned composition as an active ingredient.

In these compositions, the active ingredient is advantageously present in effective physiological doses; the previously-mentioned compositions contain in particular an effective anti-migrainous dose of at least one of the above active ingredients.

As medicaments, the above compositions can be incorporated in pharmaceutical compositions intended for digestive route.

These pharmaceutical compositions can be, for example, solid or liquid and be present in the pharmaceutical forms commonly used in human medicine, such as for example, plain or sugar-coated tablets, gelatin capsules, granules, caramels, suppositories; they are prepared according to the usual methods. The active ingredient or ingredients can be incorporated with excipients usually employed in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

Another subject of the present invention is a preparation process for a composition described above, characterized in that the active ingredient or ingredients are mixed with acceptable, in particular pharmaceutically acceptable excipients, according to methods known per se.

Another subject of the invention is a composition above for obtaining a medicament intended to be used as well anti-migrainously, i.e. for the treatment of migraines, as for obtaining a medicament intended for use as an anti-inflammatory.

A composition described above can also be presented in the form of a food supplement or a dietary or phytotherapeutic product. In these forms, it can be present in the current forms of pharmaceutical compositions, in particular those intended for OTC (over the counter) use.

All these above compositions can advantageously be combined with another active ingredient chosen from the group constituted by analgesics, antipyretics, antibiotics, anti-inflammatories, corticoids, antivirals and medicaments for cardiovascular pathologies.

The following examples illustrate the present invention.

EXAMPLE 1

Gelatin capsules were prepared corresponding to the formula

| | |
|---|---|
| Lypholized powdered hydro-alcoholic extract of white willow bark (from BIOSPHERE 99 reference BIO 3021) | 100 mg |
| Lypholized powdered hydro-alcoholic extract of aerial parts of the Fever Few (from BIOSPHERE 99 reference BIO 3010) | 100 mg |
| Copper gluconate | 1.428 mg |

The copper gluconate contains 14% $Cu^{++}$ ions or 0.20 mg $Cu^{++}$.

EXAMPLE 2

Gelatin capsules were prepared corresponding to the formula

| | |
|---|---|
| Lypholized powdered hydro-alcoholic extract of white willow bark (from BIOSPHERE 99 reference BIO 3021) | 100 mg |
| Lypholized powdered hydro-alcoholic extract of aerial parts of the Fever Few (from BIOSPHERE 99 reference BIO 3010) | 100 mg |
| Zinc gluconate | 2.000 mg |
| Magnesium gluconate | 150 mg |

EXAMPLE 3

Tablets were prepared corresponding to the formula

| | |
|---|---|
| Lypholized powdered hydro-alcoholic extract of white willow bark (from BIOSPHERE 99 reference BIO 3021) | 150 mg |
| Lypholized powdered hydro-alcoholic extract of the aerial aerial parts the Fever Few (from BIOSPHERE 99 reference BIO 3010) | 150 mg |
| Copper gluconate | 1.500 mg |

EXAMPLE 4

Vials to be taken orally were prepared corresponding to the formula

| | |
|---|---|
| Lypholized powdered hydro-alcoholic extract of white willow bark (from BIOSPHERE 99 reference BIO 3021) | 1% w/v |
| Lypholized powdered hydro-alcoholic extract of the aerial parts of the Fever Few (from BIOSPHERE 99 reference BIO 3010) | 1% w/v |
| Excipient qsp | 10 ml |

EXAMPLE 5

A cream was prepared corresponding to the formula

| | |
|---|---|
| Lypholized powdered hydro-alcoholic extract of white willow bark (from BIOSPHERE 99 reference BIO 3021) | 1% w/v |
| Lypholized powdered hydro-alcoholic extract of the aerial parts of the Fever Few (from BIOSPHERE 99 reference BIO 3010) | 1% w/v |
| Copper gluconate | 0.05% |
| Excipient qsp | 10 ml |

Pharmacological Study

1. Test of Anti-inflammatory Activity

Podal edema induced by carragheenin is used to evaulate the anti-inflammatory activity of the products tested.

Operating protocol:

The products were tested on Ico male rats and female rats (Sprague Dawley) of approximately 250 g provided by the company IFFA-CREDO.

The products tested were suspended in the hydroxypropyl methyl cellulose (HPMC).

A volume of 5 ml per kg of body weight was administered to the animals by oral route according to the protocol detained in the table below.

| Batch no. | Salix alba | Tanacetum parthenium | Copper gluconate | Quantity of excipient | Volume administered |
|---|---|---|---|---|---|
| Batch 3 | 900 mg | / | / | 15.0 ml (300 mg/5 ml) | 5 ml/kg |
| Batch 4 | / | 900 mg | / | 15.0 ml) (300 mg/5 ml) | 5 ml/kg |
| Batch 5 | 450 mg | 450 mg | / | 15.0 ml (300 + 300 mg/5 ml) | 5 ml/kg |
| Batch 6 | 450 mg | 450 mg | 4.28 mg | 15.0 ml (150 + 150 + 0.25 mg/5 ml)* | 5 ml/kg |

The control animals received either the placebo (T+), i.e. solely the HPMC, or indomethacin (T−) by oral route.

The treatment took place two hours before the experiment. One hour after oral administration of the product to be tested, all the animals received 0.2 ml of a 2% solution of carragheenin (Satia) in a 0.9% solution of sodium chloride at by injection in the right back paw ($T_0$).

The podal volume of each rat was measured using a plethysmometer. The podal edema of each animal was measured at times $T_0$, $T_0$+60 minutes, $T_0$+120 minutes, $T_0$+240 minutes.

The results were expressed in average percentages of inflammation relative to the control values ($T^+$) before the treatment and at each of the measuring times as well as in the percentage reduction of the edema compared to a control before the treatment and against each of the measuring times.

The results obtained were as follows:

RESULTS
% inflammation after 1hr, 2 hrs and 4 hrs of treatment (% compared with the control (T+))

| Control (T+) | 1 hour | 2 hours | 4 hours | Average inflammation |
|---|---|---|---|---|
| Indomethacin (T−) | 46.05 38.34 (−16.74%) | 81.92 51.85 (−36.7%) | 143.88 71.38 (−50.38%) | |
| Salix alba Batch 3 | 47.17 (+2.43%) | 85.48 (+4.34%) | 138.6 (−3.67%) | +1.03% |
| Tanacetum parthenium Batch 4 | 42.77 (−7.12%) | 69.79 (−14.18%) | 135.5 (−5.82%) | −9.04% |
| S. alba + T. parthenium (at 50%) Batch 5 | 48.14 (+4.53%) | 79.82 (−2.56%) | 130.16 (−9.52%) | −2.52% |
| Salix alba + Tanacetum parthenium + copper Batch 6 | 39.13 (−15.03%) | 62.61 (−23.57%) | 11.36 (−22.25%) | −20.28% |

"−" signifies that there was a reduction in inflammation
"+" signifies that there was an increase in inflammation Conclusions The *Salix alba* extract alone has no effect on the inflammation induced by carragheenin.

The *Tanacetum parthenium* extract alone slightly reduces inflammation (only during the first two hours after administration but this effect fades progressively).

Unexpectedly, the administration of *Salix alba* (50%) and *Tanacetum parthenium* (50%) in the presence of a metal significantly reduces the oedema induced by carragheenin from the second hour after treatment.

The anti-inflammatory activity manifests itself after the first hour of treatment and continues beyond the four hours of the duration of the test which shows a lasting activity over time.

2. Study of Anti-migrainous Activity

The anti-migrainous properties of the compositions of the present application were evaluated by studying the capacity of the product to bind itself to the β receptors involved in the migraine process.

The binding of the products tested to the β receptors was evaluated according to the technique described by Abrahamson et al. in "Biochemical Pharmacology, Vol. 37, No. 2, page 203–208, (1988).

The cellular membranes were prepared by using a piece of rat heart tissue for the analysis of the β1 receptors and of guinea-pig lung tissue for the β2 receptors. The tissues were homogenized in a centrifuge at 45000 revolutions per minute for 5 minutes. After centrifuging, the membranous pellet was diluted in 20 mM Tris buffer (Tris-HCl in 154 mM NaCl and 2 mM $MgCl_2$, pH 7.5 at 4° C.) in order to obtain a proteinic concentration of 0.6 mg/ml to 2 mg/ml for the suspensions used in the experiment with radioligands in the presence of 100 μl of Guanosine Triphosphate.

The reference compound for the β1 receptor was atenolol and for the β2 receptor the compound ICI 118.551.

The radioligand used both for the β1 receptor and for the β2 receptor was [$^3$H](−)CGP 12.177 at a concentration of 0.5 nM for the former and 0.4 nM for the latter, and the non-specific ligand alprenolol (50 μM). The incubation time was 20 mn at 25° C. in both cases.

Operating protocol:

The process was as follows:

100 mg of lyophilized extract of *S. alba* and *T. parthenium* were mixed with 1 ml distilled water (dilution 1:10) and prepared in duplicate. The tubes were centrifuged at 500 g for 5 minutes. The supernatants were collected and used as a stock solution for the following experiments.

The solution of the combination of *S. alba* and *T. parthenium*+copper as prepared by mixing 0.5 ml of solution of *S. alba* with 0.5 ml of solution of *T. parthenium* and with 0.933 mg of copper gluconate and the whole is mixed together.

To continue the studies, all the solutions were diluted to 10% for use (final dilution 1/100). All the experiments were carried out in duplicate.

The percentage inhibition of the specific radioligands obtained for the receptor studied was determined and expressed as the percentage inhibition relative to atenolol (β1) and to ICI-118551 (β2) which represent the reference compounds.

RESULTS

| Receptors | β1 | β2 |
|---|---|---|
| S. alba | −48% | −42% |
| T. parthenium | −86% | −95% |
| S. alba + T. parthenium + copper | −93% | −97% |
| Reference | Atenolol | ICI 118551 |
| IC 50 (nM) | 4.280 | 4,200 |

Conclusion

The *S. alba* extract has some affinity for the β1 receptors (−48%) and β2 receptors (−42%). The *T. parthenium* extract shows a stronger affinity for the β1 receptors (−86%) and β2 receptors (−95%). The solution containing the combination of *S. alba* and *T. parthenium* with the copper strongly inhibits the β1 receptors (−93%) and β2 receptors (−97%).

The combination of *S. alba* and *T. parthenium* with the metal is capable of inhibiting the β receptors involved in the physiopathology of the migraine by almost 100%.

3. Test of Analgesic Activity 50 male mice of 20–24 g supplied by the company IFFA-CREDO (France) were divided into 5 batches. The products studied were administered:

by oral route thirty minutes before injection of phenyl benzoquinone (PBQ): (PBQ 20 mg+alcohol 5 ml+water qsp 100 ml).

by intraperitoneal route at the rate of 0.20 ml per mouse.

The products to be tested were suspended in the excipient HPMC (hydroxypropyl cellulose methyl).

The animals were treated as below:

| BATCH | DOSE (mg/kg) | VOLUME (ml/kg) |
| --- | --- | --- |
| 1. Control (HPMC) | 0 | 10 |
| 2. Aspirin | 100 | 10 |
| 3. Salix alba | 150 | 10 |
| 4. Tanacetum parthenium | 150 | 10 |
| 5. S. alba + T. parthenium + copper | 75 + 75 + 0.2 | 10 |

Aspirin was used as the reference analgesic product.

PBQ induces abdominal cramps indicating the intensity of the pain. The number of cramps per mouse was measured 1 hr and 2 hrs after administration of the product tested (30 mn and 1 hr 30 minutes after injection of PBQ).

RESULTS

The results were expressed as the percentage:

$$\frac{\text{Number of cramps of the control batch - number of cramps of the treated batch}}{\text{Number of cramps of the control batch}} \times 100$$

Table of results: number of cramps over a period of 10 minutes:

Conclusion

The aspirin used as an analgesic reference product reduces the abdominal cramps induced by the injection of PBQ by 33% and 55% respectively fo 60 mins and 120 mins after administration.

The *Salix alba* extract alone at a dose of 150 mg/kg slightly reduces the number of cramps (13% and 15% respectively after 1 hr and 2 hrs).

The *Tanacetum parthenium* extract alone has no effect during the first hour of treatment; on the other hand, it shows a slight analgesic activity (11%) at T=2 hrs.

The combination of *Salix alba* extract (50%), *Tanacetum parthenium* extract (50%) and copper produces a large increase in analgesic effects of the two extracts tested alone.

These results show that although *Salix alba* alone or *Tanacetum parthenium* alone do not have analgesic activity, combining them with copper ($Cu^{++}$) brings about a useful analgesic effect.

4. Toxicology Study

The acute toxicity of the dry extract of white willow bark (*S. alba*)—dry extract of Feverfew (*T. parthenium*)—copper gluconate was evaluated in the following proportions: 15 g—15 g—142.8 mg (5 g in 20 ml water) for the Ico rat (Sprague Dawley) at a dose of 2 ml/kg administered by oral route in one dose. The morbidity examinations were carried out 15 mn, 1, 2, and 4 hours after intubation then daily until day 14.

The lethal dose 50 (LD 50) of the product tested is more than 2 g/kg by oral route in the rat.

What is claimed is:

1. A composition of salicin or an active derivative thereof, and a parthenoid, or plant materials or plant extracts containing the two active ingredients, and further comprising at least one metal of copper, zinc or magnesium in trace element amount of less than 1 part per 100, in a unit dosage form in an amount effective for the treatment of migraine.

2. A composition according to claim 1, wherein said plant materials or extracts comprises a plant material or extract of the Tanacetum genus and a plant material or extract of the Salix genus.

3. A composition according to claim 1, wherein said extracts are dry extracts from dried and ground parts of the plants.

4. A composition according to claim 1, wherein said plant materials or extracts comprises a plant material or extract of the Tanacetum genus and a plant material or extract of the Salix genus.

5. A composition according to claim 4, wherein said extracts are dry extracts from dried and ground parts of the plants.

6. A composition according to claim 1, wherein said metal is copper.

7. A composition according to claim 6 wherein said plant materials or extracts comprises a plant material or extract of the Tanacetum genus and a plant material or extract of the Salix genus.

8. A composition according to claim 6, wherein said extracts are dry extracts from dried and ground parts of the plants.

9. A pharmaceutical composition as defined in claim 1 further comprising a pharmaceutically acceptable excipient.

10. A method for the treatment of migraine, comprising administering to a patient in need of said treatment an amount effective for said treatment of a composition according to claim 1.

11. A method for the treatment of migraine, comprising administering to a patient in need of said treatment an amount effective for said treatment of a composition according to claim 2.

12. A method for the treatment of migraine, comprising administering to a patient in need of said treatment an amount effective for said treatment of a composition according to claim 3.

13. A method for the treatment of migraine, comprising administering to a patient in need of said treatment an amount effective for said treatment of a composition according to claim 6.

* * * * *